United States Patent [19]

McKenna

[11] Patent Number: 5,255,687
[45] Date of Patent: Oct. 26, 1993

[54] ZERO DEAD SPACE RESPIRATORY EXERCISE VALVE

[76] Inventor: Charles L. McKenna, 9744 1st St., Gerber, Calif. 96035

[21] Appl. No.: 827,085

[22] Filed: Jan. 21, 1992

[51] Int. Cl.$^5$ ............................ A62B 9/02; A61B 5/08
[52] U.S. Cl. ..................................... 128/730; 137/512; 137/855; 128/205.24; 482/13; 22/84
[58] Field of Search ........... 128/716, 725, 730, 202.29, 128/203.11, 205.24, 206.15, 207.16; 137/102, 512, 855, 908; 482/13; 422/84

[56] References Cited

U.S. PATENT DOCUMENTS

| | | | |
|---|---|---|---|
| 3,902,516 | 9/1975 | Rudolph | 137/102 |
| 4,111,228 | 9/1978 | Simionescu | 137/512 |
| 4,292,978 | 10/1981 | Guth | 128/730 |
| 4,456,016 | 6/1984 | Nowacki et al. | 128/725 |
| 4,538,620 | 9/1985 | Nowacki et al. | 128/207.16 X |
| 4,601,465 | 7/1986 | Roy | 128/725 X |
| 4,635,647 | 1/1987 | Choksi | 128/725 X |
| 4,942,873 | 7/1990 | Irwin et al. | 128/205.24 X |

*Primary Examiner*—Lee S. Cohen
*Assistant Examiner*—Samuel Gilbert

[57] ABSTRACT

A pulmonary valve for use with fitness level respiratory testing equipment, having a tubular silicone rubber body member. Formed at one end of this member is a mouth seal which is subsequently inserted into a subjects mouth. In the superior surface of the tubular body member is found the inhalation ports, these ports allow for air passage during inhalation. Within the tubular body member is housed two valve membranes, one for inhalation and one for exhalation. During inhalation, the inhalation membrane opens, creating an airflow passage-way directly to a subjects's mouth cavity. During exhalation the inhalation membrane closes shut and the exhalation membrane opens thus creating a second and separate airflow passage-way, at the end of exhalation the exhalation membrane closes shut, thus completing one respiration cycle. Because of the unique membrane design there is found no equipment dead space. The pulmonary valve may be equipped with an auxiliary oxygen tank adaptor sleeve which is fitted to the outside of the tubular body member. This adaptor sleeve will accept a hose connecting at one end and creates a gas airflow passage-way to the inhalation ports found in the superior surface of the tubular body member.

4 Claims, 5 Drawing Sheets

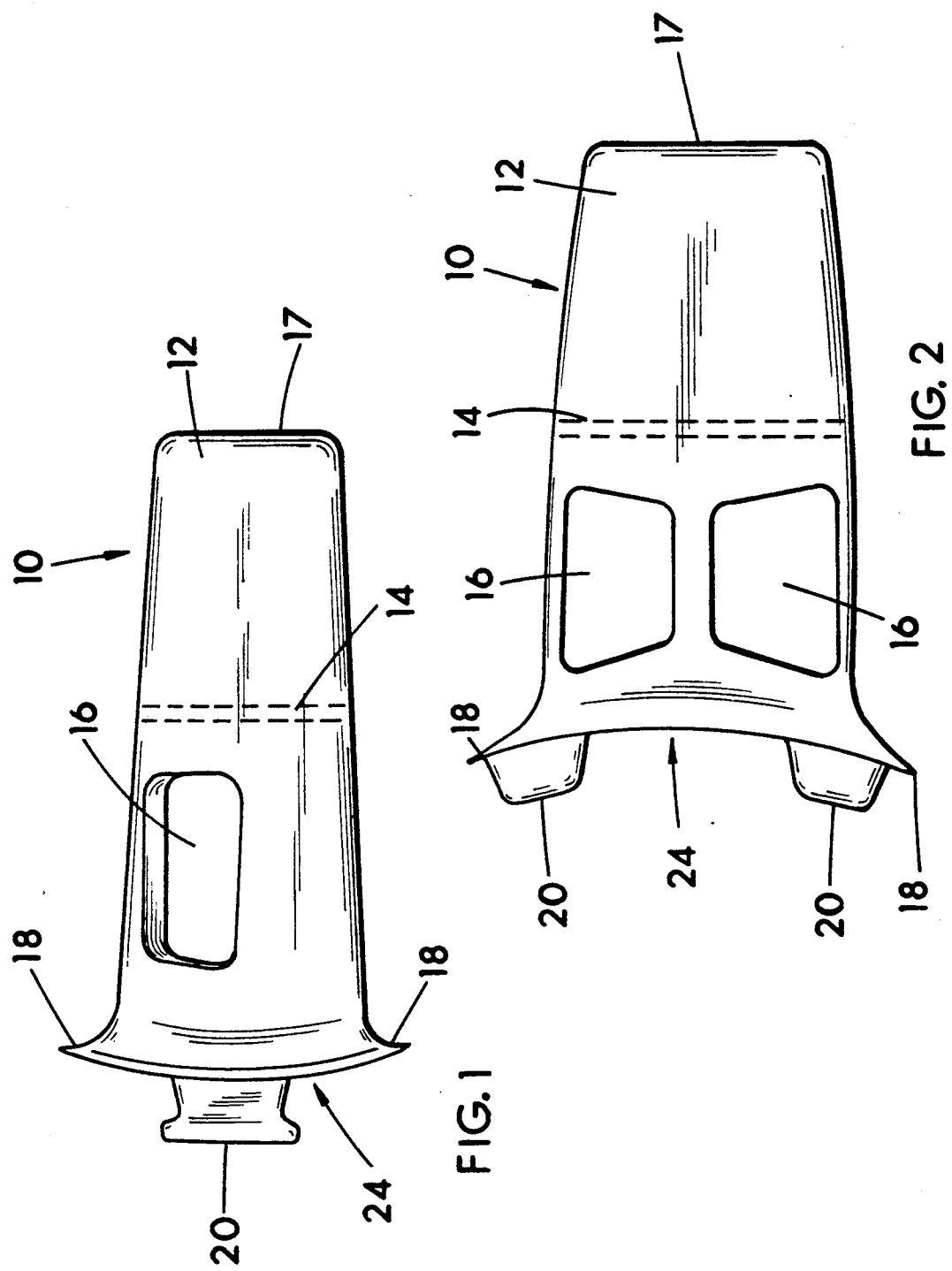

ZERO DEAD SPACE RESPIRATORY EXERCISE VALVE

BACKGROUND OF INVENTION

1. Field of the Invention

This invention relates to analyzing equipment used in the field of exercise physiology, with the present invention being particularly directed towards the receiving and directing of differing lung gases for direct computer analyses, during vigorous exercise.

2. Description of the Prior Art

There are currently valves used for obtaining this particular type of analysis of lung gases during *vigorous exercises*. Also there are valves used in respiratory therapy designed specifically for directing lung gases at very low volumes of air per minute, and as therapy for people with lung disorders, however, valves for directing lung gases for direct computer analysis at very large volumes of air per minute without having a dead space do not exist. The present invention is designed to provide for this application.

SUMMARY OF INVENTION

Therefore in practicing my invention I have provided a high volume zero dead space valve device for the directing of oxygen and other gases into a subjects mouth cavity during the inhalation faze of respiration. There after the device subsequently directs lung gases towards equipment and computers for analysis, during the exhalation faze of respiration. With my device a valve cartridge made of plastic and having two thin membranes for the directing of air flow, is inserted into a silicon rubber mouthpiece. When inserted the inhalation ports of the valve cartridge and the mouthpiece body are aligned in such a way as to indicate a common inhalation port. One end of the mouthpiece is then inserted into a mouth cavity of a subject. The other end of the mouthpiece can then be attached to analytical equipment via a hose or through electronic sensors. In use, breathable gases are allowed to enter a mouth cavity through the common inhalation ports which are located in the superior body of the valve device. The inhaled gases then force open the inhalation membrane which is covering the inhalation port from the inside of the valve cartridge. The inhalation membrane collapses down, thus opening the common ports. The gases can now flow to the mouth and subsequently to the lungs. As these gases are forced out of the lung cavity, the inhalation membrane closes off the inhalation ports so that the lung gases can not escape back into the room. The device now only allows the exhaled gases to flow past the exhalation membrane which collapses down and out of the way due to the force of exhalation, allowing the gases to exit the valve device via the exhalation port. After the gases have exited the device, the exhalation membrane shuts off the exhalation port and the cycle repeats.

The invention is comprised in three components. One having a cartridge which houses the inhalation and exhalation membranes, one being the mouth piece which houses the cartridge and one being an optional intake hose attachment for the connecting of external gas tanks. Therefore the principle object of the invention is to provide an exercise respiratory valve with no dead space.

Another object of the invention is to provide a disposable mouth piece to decrease the chance of spreading diseases.

A further object of my invention is to provide a less bulky device, which eliminates the need for heavy harnesses used in prior art.

A still further object of the invention is to provide a place for either hose connected analysers or electronically connected analysers.

Other objects and advantages of the present invention will become understood by reading discriptions of numbered parts in the specification and comparing the described parts with similarly numbered parts illustrated in the drawings.

BRIEF DESCRIPTION OF THE DRAWINGS

As shown in the drawings:

FIGS. 1 and 2 are a perspective illustration of the disposable rubber mouth piece.

FIG. 4 shows the inhalation membrane in its closed and open position and FIG. 5 shows the exhalation membrane in its closed and open position.

DESCRIPTION OF THE PREFERRED EMBODIMENT

Figure 3:
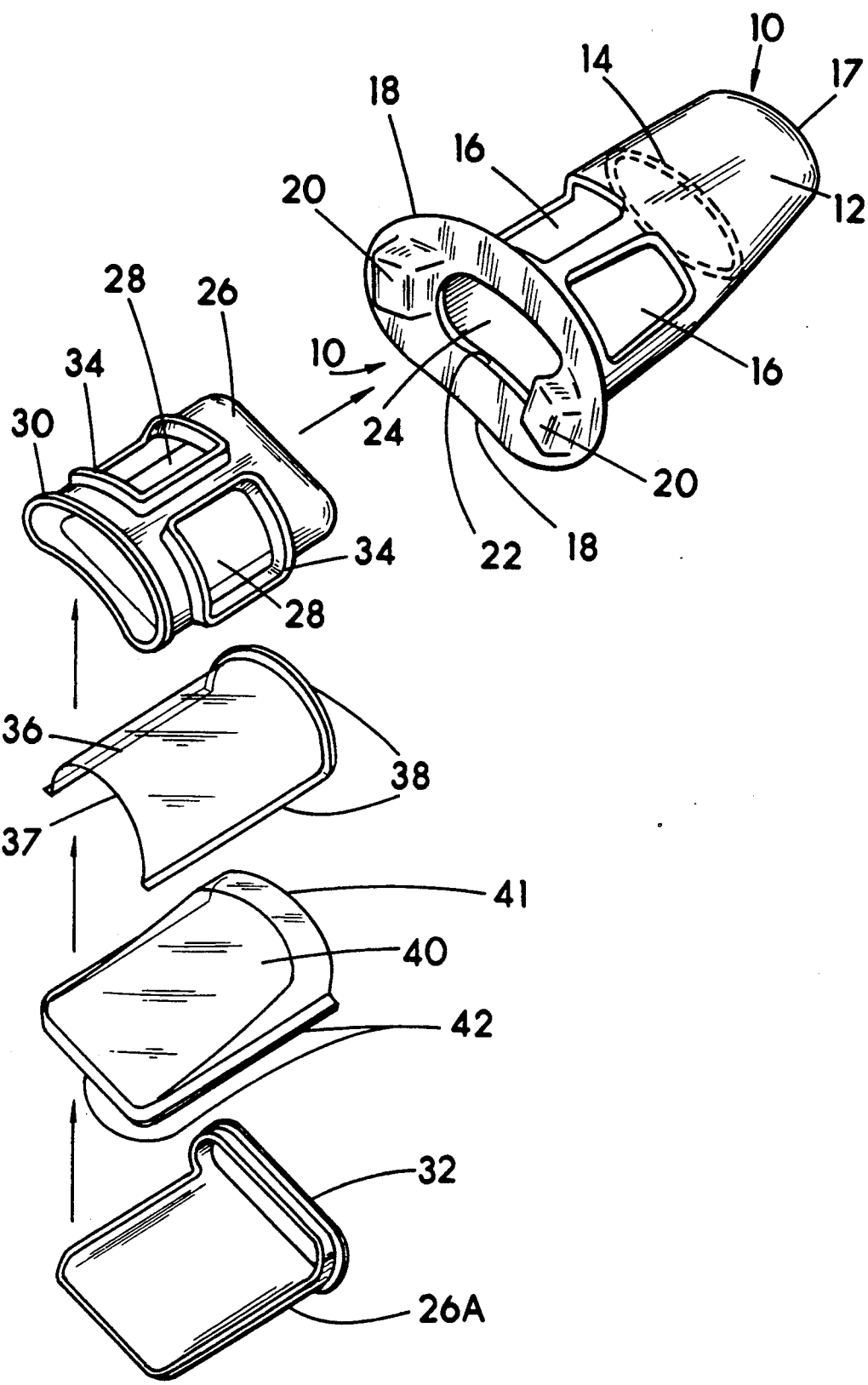
FIG. 3 is an exploded view showing the relationships of the two valve membranes to their cartridge housing and that cartridge housing's relationship to its disposable mouth piece.

Referring now to the drawings at FIG. 1 and 2 where disposable rubber mouth piece 10, according to the invention, is illustrated. It is shown as a side view FIG. 1 and a top view FIG. 2. 12 show the body of the mouth piece, it is made of a medical grade silicon rubber, it is of one piece construction having a mouth seal, 18, which fits into a mouth cavity as in FIG. 8, also at this end are the bite tabs, 20, which allows for the biting down of teeth, which helps hold the mouth piece 10 in place. 24 indicates the cartridge insert opening this opening allows for the insertion and placement of the cartridge housing FIG. 3, 26. The mouth piece inhalation port, 16, serve a duel purpose one, to allow air flow into the lung cavity and two they also serve as receiving cavities for the valve cartridge inhalation port flanges 34 FIG. 3, the dotted line 14 indicates the rear flange cartridge receptor groove which is cut about half way down the inside of the mouth piece body 12 this groove receives flange 32 of the valve cartridge housing 26A FIG. 3 and forms a seal between the valve cartridge housing 26 FIG. 3 and the mouthpiece 10. Lastly in FIG. 1 and 2 is exhalation port 17. This port allows for the insertion of various fittings that are present on different types of analyzer hoses, 54 FIG. 8, and airflow meter devices, 55 FIG. 8.

Referring to FIG. 3, the cartridge housing 26 and 26A is shown in two parts having the same number, however in its completed form the cartridge housing 26 and 26A are one unit made of a plastic and is a component according to the invention. The front of the cartridge 26 is denoted by a valve cartridge front flange 30, the top of cartridge 26 is denoted by a set of valve cartridge inhalation port flanges 34, and the back of the cartridge is denoted by a valve cartridge housing rear flange 32 found on valve cartridge housing completion 26A. These three flanges 30, 34, and 32 insert into their counter parts located in mouth piece 12. Front cartridge flange receptor groove 22 receives valve cartridge housing front flange 30, inhalation ports 16 receive valve cartridge inhalation port flanges 34 and rear flange cartridge receptor groove 14 receives valves cartridge housing rear flange 32 found on valve cartridge housing completion 26A. Both front and rear valve cartridge housing flanges 30 and 32 are continuous around their respective ends of the valve cartridge housing 26 and 26A as are there counter parts front and rear receptor grooves 22 and 14 respectively in mouth piece 12. All of the flanges 30, 34, and 32 help to hold the cartridge housing 26 securely to the inside of mouthpiece 12.

The valve cartridge housing 26 and 26A also encapsulates the two valve membranes 36 and 40. Valve membrane 36 is the inhalation membrane it is made of a very thin silicon rubber sheet and molded in a convex shape having and inhalation membrane flange 38 on all its edges except for the leading edge 37 which has no flange at all. Exhalation membrane 40 is made of the same material as 36 however it is molded in a convex shape at its trailing edge 41 and tapers in a wedge shape to its exhalation membrane flange 42 which runs along its front edge and continues along its sides. When the valve cartridge housing 26 and 26A are complete inhalation and exhalation membrane 36 and 40 are sandwiched between valve cartridge housing 26 and 26A.

Figure 5:
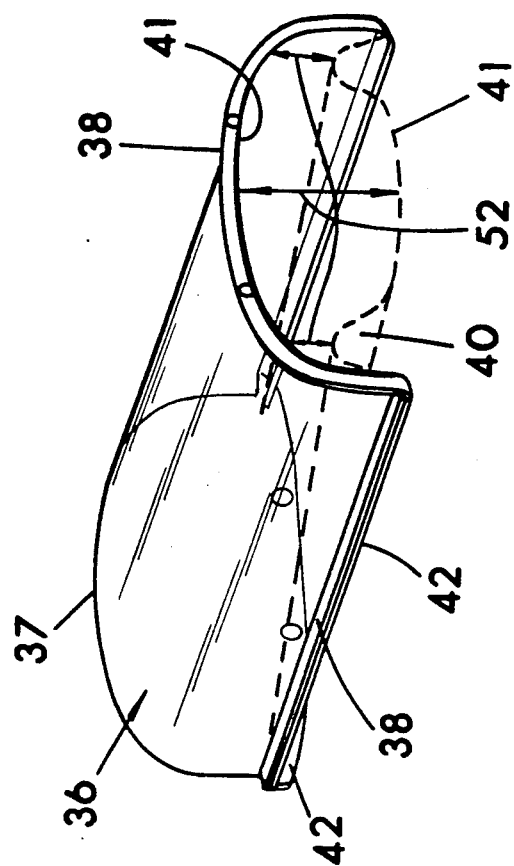
FIGS. 4 and 5 are perspective illustrations of just the valve membranes and how they collapse when they are in use; the cartridge which houses these membranes is not shown.
Figure 4:
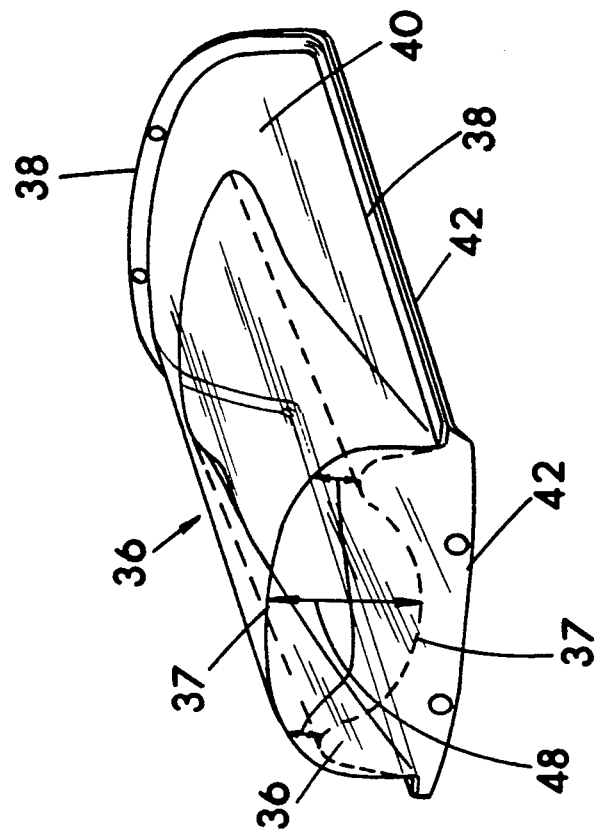

Referring to FIGS. 4 and 5 in these perspectives only the inhalation and exhalation membranes 36 and 40 respectively are viewed. They have been placed together in their proper location to each other and enlarged for easier viewing. FIG. 4 is primarily concerned with the movement of the inhalation membrane 36 when air is inhaled this membrane 36 collapses as designated by dotted lines. Inhalation membrane movement indicators 48 show the direction of movement of the leading edge 37 of the inhalation membrane, as a person begins to inhale a vacuum is produced in the lungs because of the higher pressure of the room air the inhalation membrane 36 is forced open air is allowed to pass through the inhalation membrane ports 28 FIG. 3 and into lungs. As air pressure is equalized between the lungs and the room the inhalation membrane 36 closes off the inhalation membrane ports 28 FIG. 3 so that no lung gases can escape back into the room. Instead the lung gases are directed toward the exhalation membrane 40 the increased air pressure on membrane 40 forces it open as indicated by dotted lines, the exhalation membrane movement indicators 52 show the direction of movement the trailing edge 41 of the exhalation membrane 40. Lung gases are now allowed to pass out of lungs and flow to the lung gas analyzer 58 via the analyzer hose 56 and adaptor 54 all of which are shown in FIG. 8. As lung gases are finally exhausted, exhalation membrane 40 slaps shut and the cycle repeats. It should be noted that the trailing edge 41 of exhalation membrane 40 conforms to the rear underside of inhalation membrane 36, this creates a seal between the two membranes, this seal is made even greater by lower pressure caused by inhalation and is breached by greater pressure caused by exhalation. Along with the explanations for FIGS. 4 and 5 are schematic side views FIGS. 6 and 7, these figures also show relationships between inhalation membrane 36 and exhalation membrane 40.

Figure 6:
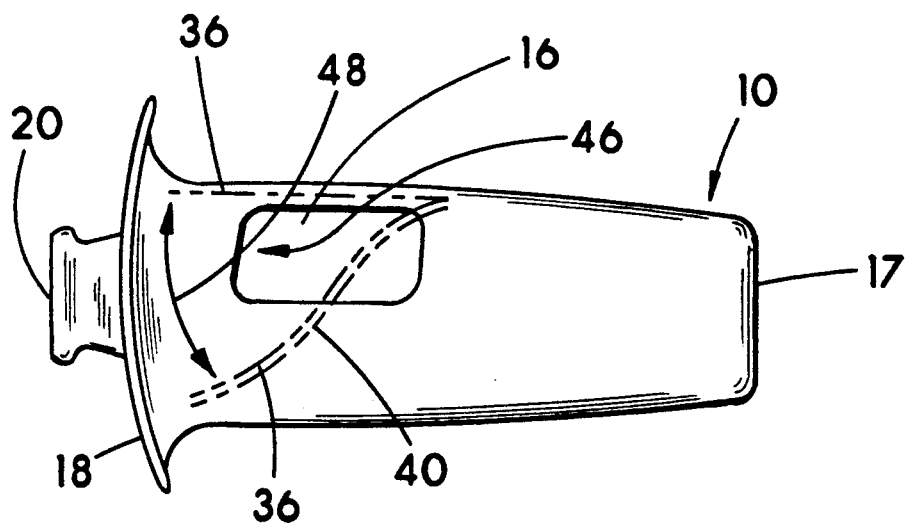
FIGS. 6 and 7 are schematic drawing showing by simple lines, the opening and closing of the two valve membranes during inhalation, (top FIG. 6), and exhalation, (middle FIG. 7). Arrows indicate direction of air flow.

In referring to FIG. 6 we see the movement of inhalation membrane 36 as it moves from its closed position to its open position and back as indicated by movement indicators 48. Also shown is the air steam indicator arrow 46 which shows the direction of air flow when inhalation membrane 36 is open, air flow is going into the lungs via inhalation port 16.

Figure 7:
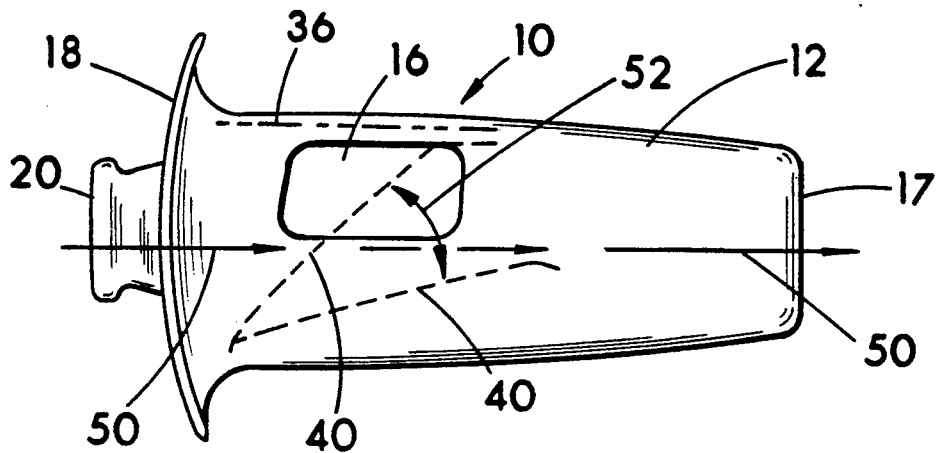
Figure 8:
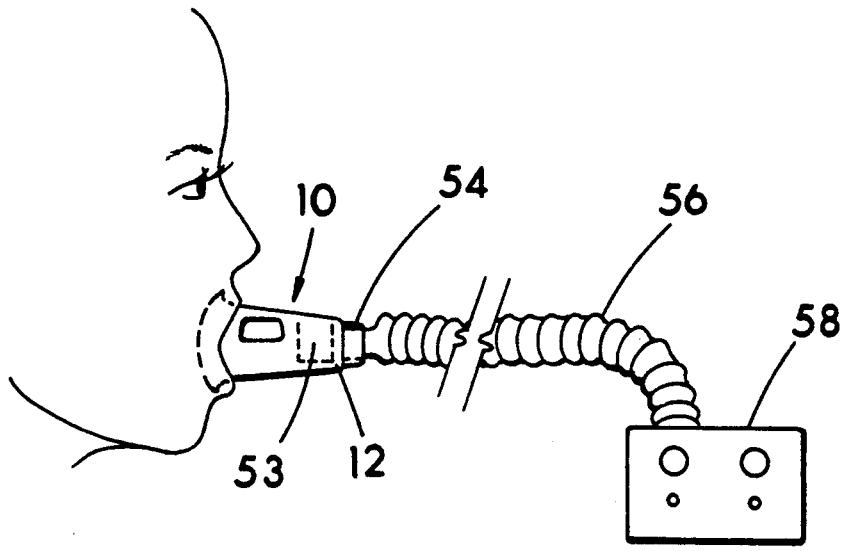
FIG. 8 shows the mouth piece inserted into the mouth cavity at one end and an analyser hose inserted at the other end.

In referring to FIG. 7, this shows the direction of air flow from the lungs to the analyzer hose 56 FIG. 8 as indicated by air stream indicators 50. At the same time the exhalation membrane 40 moves from its closed position to its open position as indicated by movement indicators 52.

In referring to FIG. 8 a side view of the mouth piece 12, the mouth piece 12 is inserted into a mouth cavity. At the opposite end of the body of the mouthpiece 12, an analyzer hose is fitted into the exhaust port opening 17 FIG. 1. The dotted square box indicates area 53 electronic sensor implant site. where electronic sensors can be punched through the body of the mouthpiece 12. When electronic sensors are used an airflow meter 55 is inserted in place of the analyzer hose 56 and hose adaptor 54.

Figure 9:
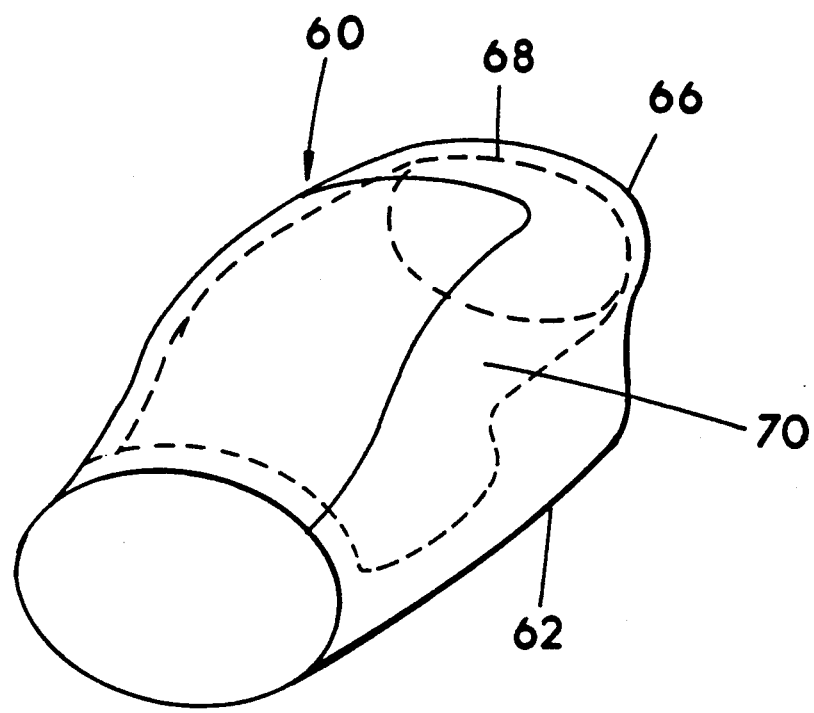
FIG. 9 is a perspective illustration of the optional auxiliary oxygen tank adaptor sleeve.
Figure 10:
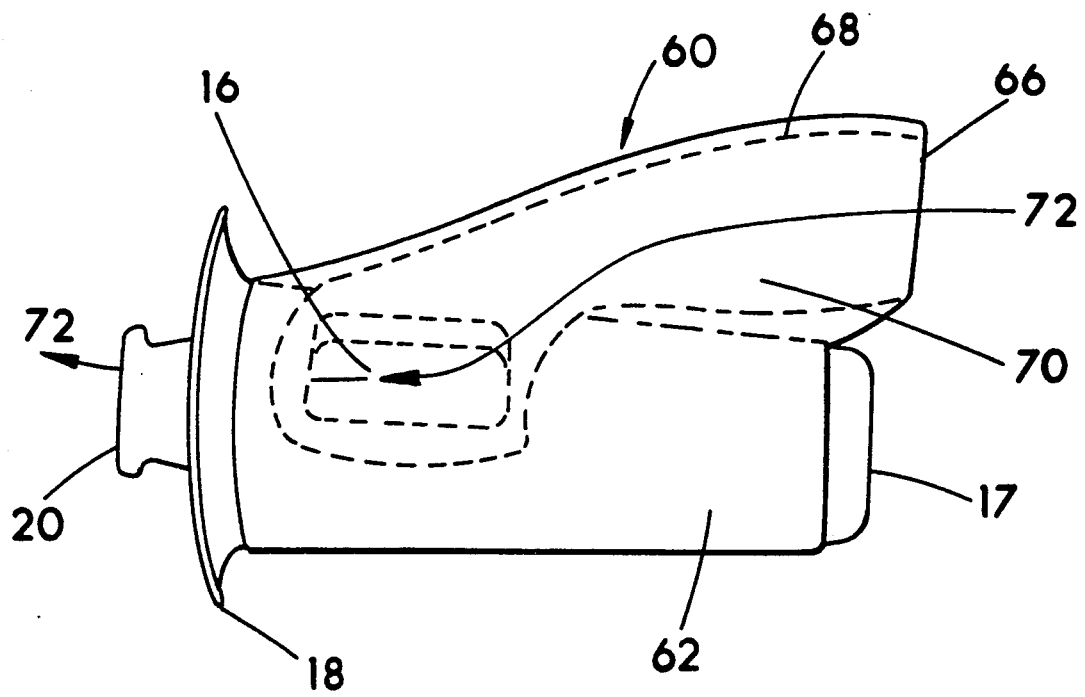
FIG. 10 is a side view of the auxiliary oxygen tank adaptor sleeve in place over the side view of the mouth piece.

In referring to FIGS. 9 and 10 both deal with the auxiliary oxygen tank adaptor sleeve 60. This apparatus is only used in cases where pure gases are to be used such as pure oxygen. The sleeve 60 slips over the body of the mouthpiece 12 FIG. 1 completely covering the mouth piece inhalation ports 16. The sleeve 60 is of one piece construction made of the same material as the mouthpiece 12 FIG. 1. In referring to FIG. 10 it is held snug to the body of the mouthpiece 12 by a wide elastic strap 62 the sleeve 60 has and upper rear hose receptor port 66 this port receives a hose from an auxiliary oxygen tank. The dotted lines 68 indicate the cavity 70 in which oxygen travels to the inhalation ports 16 the arrow 72 indicates the direction of air flow. It should be known that the auxiliary oxygen tank adaptor sleeve 60 is only used in special cases and for the most part is not attached as in FIG. 10.

Although I have described an embodiment of my invention with considerable detail in the foregoing specification and have illustrated it extensively in the drawings, it is to be understood that I may practise variations in the invention which do not exceed the scope of the appended claims and that variations of my invention practiced by others which fall within the scope of my claims, I shall consider to be my invention.

What is claimed:

1. Respiratory level testing system comprising: a mouthpiece having a passageway with first and second open ends, an opening through a surface of said mouthpiece communicating with said passageway between said open ends and means for receiving a valve cartridge housing in said passageway;

a valve cartridge housing; said valve cartridge housing is removably inserted into said passageway through said first open end and secured by said means for receiving;

first and second valve means for forming first and second airflow passageways between said opening and said first open end and between said first open end and said second open end respectively, said valve means having zero deadspace and being inserted in said valve cartridge housing; and an adapter sleeve means for selectively connecting the mouthpiece to a hose from an auxiliary oxygen tank, said adapter sleeve means having elastic strap means for removably securing said adapter sleeve means to said mouthpiece, said adapter sleeve means being secured to said mouthpiece such that a first open end of said adapter sleeve means overlies said opening through said surface of said mouthpiece and a second open end of said adapter sleeve means is adapted to receive said hose from said auxiliary oxygen tank.

2. The respiratory testing equipment system of claim 1 wherein said means for receiving comprises a first flange receptor groove formed circumferentially around an inside surface of said mouthpiece between said first open end and said opening and a second flange receptor groove formed circumferentially on said inside surface of said mouthpiece midway between said first open end and said second open end wherein said opening is between said first and second flange receptor grooves.

3. The respiratory testing equipment system of claim 2 wherein said valve cartridge housing further comprises first, second, and third flanges, wherein said first flange engages said first flange receptor groove, said third flange engages said second flange receptor groove, and said second flange engages said opening through said surface.

4. The respiratory testing equipment system of claim 3 wherein said first and second valve means comprise first and second valve membranes wherein said first valve membrane has a concave shape and overlies said second valve membrane which has a wedge shape.

* * * * *